(12) United States Patent
Roth et al.

(10) Patent No.: US 6,355,023 B1
(45) Date of Patent: Mar. 12, 2002

(54) CLOSED SYSTEM ACCESS DEVICE

(75) Inventors: Lindsay Roth, Waterbury; Susan Gibbons, Southington, both of CT (US)

(73) Assignee: Gaylord Hospital, Wallingford, CT (US)

( * ) Notice: Subject to any disclaimer, the term of this patent is extended or adjusted under 35 U.S.C. 154(b) by 0 days.

(21) Appl. No.: 09/440,391

(22) Filed: Nov. 15, 1999

(51) Int. Cl.⁷ ................................................ A61B 5/32
(52) U.S. Cl. ...................... 604/411; 604/905; 604/533
(58) Field of Search ..................... 604/533, 198, 604/263, 905, 408–415, 244, 83, 86, 192, 199, 256, 239, 264, 272, 537, 538; 128/919; 141/329, 369, 370, 374, 382, 383; 600/573, 576, 577, 579, 580

(56) References Cited

U.S. PATENT DOCUMENTS

| | | |
|---|---|---|
| 3,826,261 A | 7/1974 | Killinger |
| 3,993,063 A | 11/1976 | Larrabee |
| 4,576,211 A | 3/1986 | Valentini et al. |
| 4,759,756 A * | 7/1988 | Forman et al. ............. 604/413 |
| 4,943,283 A | 7/1990 | Hogan |
| 4,950,260 A | 8/1990 | Bonaldo |
| 4,998,925 A | 3/1991 | Al-Sioufi et al. |
| 5,088,985 A | 2/1992 | Deras |
| 5,139,483 A | 8/1992 | Ryan |
| 5,330,450 A | 7/1994 | Lopez |
| 5,533,993 A | 7/1996 | Maier |
| 5,626,567 A * | 5/1997 | Gmeiner ..................... 604/236 |
| 6,238,372 B1 * | 5/2001 | Zinger et al. ............... 604/246 |

* cited by examiner

Primary Examiner—Richard K. Seidel
Assistant Examiner—Cris Rodriquez
(74) Attorney, Agent, or Firm—Cantor Colburn LLP

(57) ABSTRACT

The above-discussed and other drawbacks and deficiencies of prior art are overcome or alleviated by the closed system access device of the present invention. The closed system access device provides a tool for managing fluid transactions that ensures the sterility of a needle, prevents exposure to toxic or hazardous medicines, and protects against needle stick by completely encasing the needle in a housing. The device allows for a protected needle withdrawal of blood, injection of medicine and transfer of fluids by use of an unexposed, internal needle which inhibits contamination and prevents contact with the transferred blood and/or medicine.

14 Claims, 8 Drawing Sheets

CLOSED SYSTEM ACCESS DEVICE

BACKGROUND OF THE INVENTION

1. Field of Invention

The invention relates generally to a device for the administration of transactions involving bodily fluids, and particularly, to a housing with an encased needle which, when used in conjunction with any one of a variety of common access devices, minimizes or eliminates the health care professional's risk of needle stick while protecting the patient against needle contamination during the collection and transfer of bodily fluids and the injection of medication and the like.

2. Description of Prior Art

Increased occurrence of blood-borne pathogens such as HIV and hepatitis have led healthcare institutions to search for safety devices which decrease an employee's risk of exposure to patient blood. The prevalence of needles in traditional phlebotomy and other procedures subjects health care workers to a significant threat of such exposure through sharps incidents, i.e. needlesticks. Each year, throughout the nation's healthcare facilities, thirty sharps injuries occur per one hundred occupied hospital beds. Seventyfour percent of 'high risk' sharps injuries, those injuries associated with blood filled needles, are incurred by health care practitioners in relation to blood drawing procedures.

Traditional blood drawing procedures involve various apparatus and methods. One common method entails the use of a hypodermic syringe. A conventional hypodermic syringe includes a syringe body, a piston member, a hypodermic needle, and a needle cap. With the piston member in a decompressed position, blood is drawn through the needle into the syringe body while the needle is inserted directly into the vein or into a tube connected to a second needle that is inserted in the vein. A second common method of drawing blood involves a blood bag system. A conventional blood bag system consists of a length of tubing connected to a first needle at one end and to a bag at the other. The first needle is inserted into a vein to draw blood from the vein, through the tube, into the bag or test tube or other collection device.

Due to the spread of infectious diseases, most syringes and needle assemblies used today are designed for one use only and immediate disposal. Although disposal of syringes and needle assemblies immediately after they are used reduces human exposure to contaminated needles, it does not eliminate all of the problems associated with traditional blood draw methods. Contact with a needle before it is used can contaminate the needle and hence any medication which passes through it, thus threatening the patient. Contact with a needle after it is used can result in the transmission of disease from patient to health care practitioner. Contact with toxic or hazardous medication contained in the needle, syringe, or tube threatens the safety of both practitioner and patient.

Various technologies have addressed the need to protect health care practitioners and patients from the risks associated with the use of exposed needles in phlebotomy procedures. A safety syringe, discussed fully in U.S. Pat. No. 5,088,985 ('985) and incorporated herein by reference, describes a syringe device having a safety apparatus for shielding the needle and another apparatus for removing said needle after use. A blood collecting apparatus, discussed in U.S. Pat. No. 4,943,283 ('283) and incorporated herein by reference, describes a tube arrangement to be used with a blood bag wherein needles used for piercing a vein and for filling test tubes with blood for various screening tests are safety shielded. U.S. Pat. No. 4,576,211 ('211), incorporated herein by reference, teaches a device which facilitates the safe withdrawal of toxic or otherwise hazardous medicine from a bottle into a syringe.

These and other technologies fail to adequately protect patients and practitioners from the hazards associated with needle use in phlebotomy procedures. Despite their safety features, the devices referred to above still require the practitioner to handle needles before and after usage and also expose both the practitioner and patient to the risk of contact with hazardous medicine and bodily fluids. The device described in the '985 patent provides a member for 'hands-free' removal of a used needle, however, the health care employee still encounters the risk of needlestick when inserting a used needle into the removing member. Both devices of the '985 and '283 patents provide needle shields to protect the user from unintended needle contact. However, these shields are slidably mounted and thus are only effective when engaged. When the needle is disengaged the practitioner is subject to needlestick and the patent is endangered by the threat of needle contamination. Further, neither the '985 nor the '283 patents provide protection against contact with medicine which may be toxic or hazardous in nature. The device discussed in the '211 patent allows for the safe drawing of such medicine into a syringe but no protection is offered in transferring the medicine to the patient and injecting it into a vein.

Thus the need has arisen for a device to be used in venous transactions which protects both health care practitioners and patients from the risks inherent in phlebotomy procedures by protecting against needlestick, ensuring the sterility of needles, and preventing contact with dangerous medicines.

Summary of the Invention

The above-discussed and other drawbacks and deficiencies of prior art are overcome or alleviated by the closed system access device of the present invention. The closed system access device provides a tool for managing fluid transactions that ensures the sterility of a needle, prevents exposure to toxic or hazardous medicines, and protects against needle stick by completely encasing the needle in a housing. The device allows for a protected needle withdrawal of blood, injection of medicine and transfer of fluids by use of an unexposed, internal needle which inhibits contamination and prevents contact with the transferred blood and/or medicine. In an exemplary embodiment, the device comprises a protective shielding assembly including a housing having an outer wall and an intermediate wall extending between the outer wall of the housing. The intermediate wall partitions the housing into a first section and a second section. A first needle extends from the first section to the second section of the housing through the intermediate wall, wherein the first needle having a first portion disposed in the first section and a second portion disposed in the second section. The assembly also includes a first connector disposed in the second section about the first needle for connecting a first member to the first needle in the second section and a second needle is disposed at least partially in the first section of the housing and extends through the outer wall of the housing. The second needle preferably terminates in a needle-less fluid port in which the fluid port is for fluid connection to a second member. The assembly further includes a removable guide liner having a body including a first end, an opposing second end, and an outer wall complementary to the outer wall of the housing so that the removable guide liner is intimately received within the first section of the housing. The body has a guide slot formed therein where the guide slot extends from the first end to an end wall proximate the second end. The end wall includes an opening formed therein for receiving the first portion of the first needle and a portion of the second needle so that the first portion and the second needle extend into the guide slot. The guide slot receives a third member which is fluidly connected to the first and second needles so that a fluid transfer may occur between the third member and at least one of the first and second members where the first and second needles are fully encased within the housing so as to protect the user from contact therewith.

BRIEF DESCRIPTION OF THE DRAWINGS

Referring now to the drawings wherein like elements are numbered alike in the several Figures.

DETAILED DESCRIPTION OF THE PREFERRED EMBODIMENTS

Figure 1:
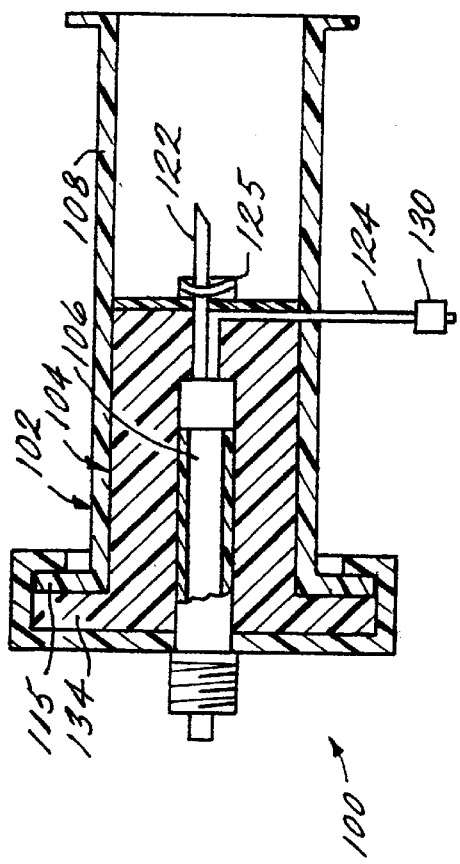
FIG. 1 is a cross-sectional side elevational view of a device in an assembled state in accordance with the present invention.
Figure 2:
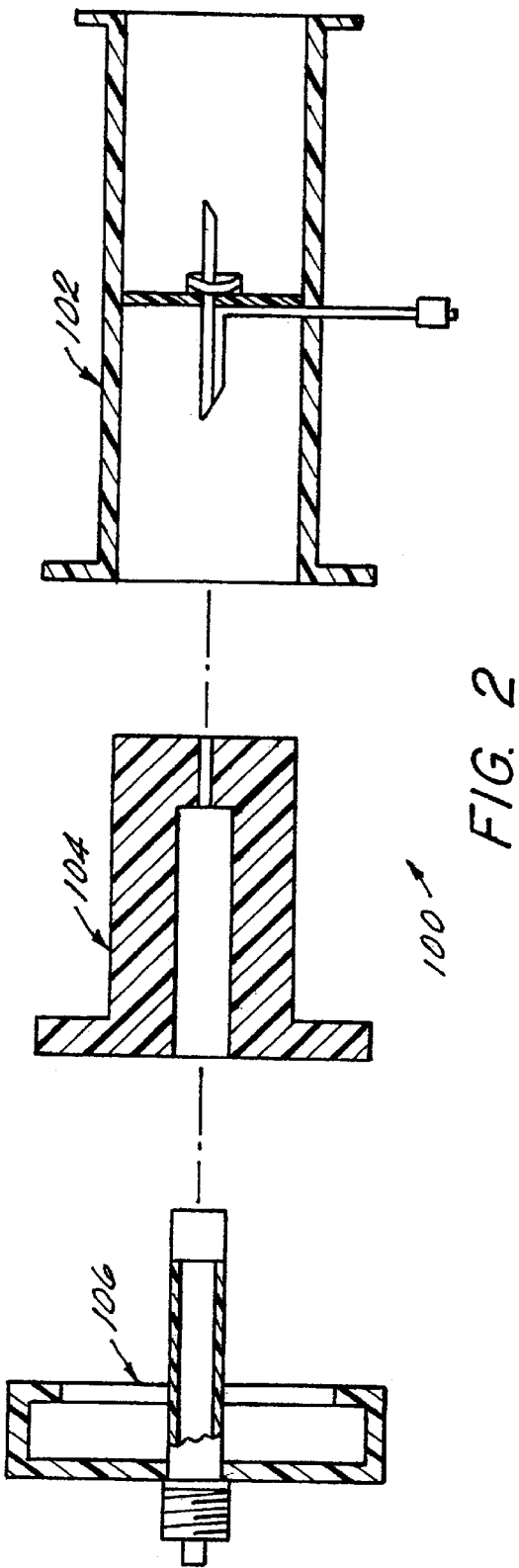
FIG. 2 is an exploded cross-sectional side elevational view of the device of FIG. 1.
Figure 3:
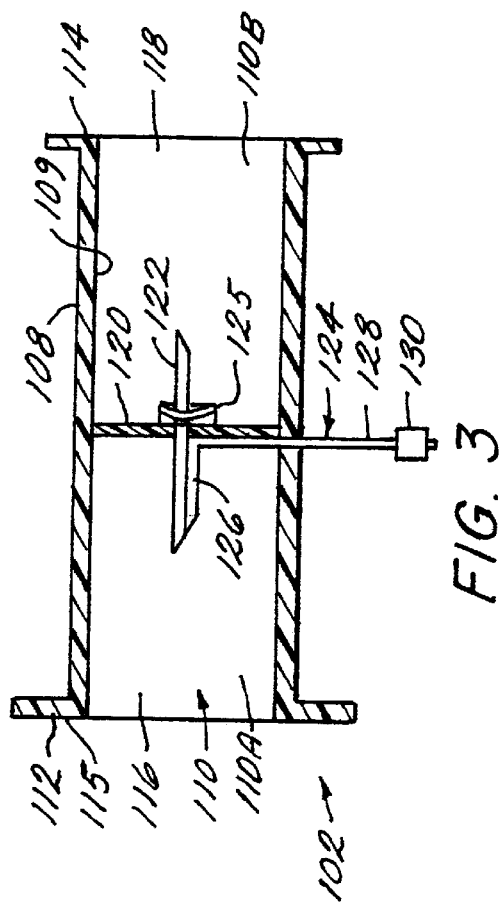
FIG. 3 is a cross-sectional side elevational view of a housing assembly of the device of FIG. 1.
Figure 5:
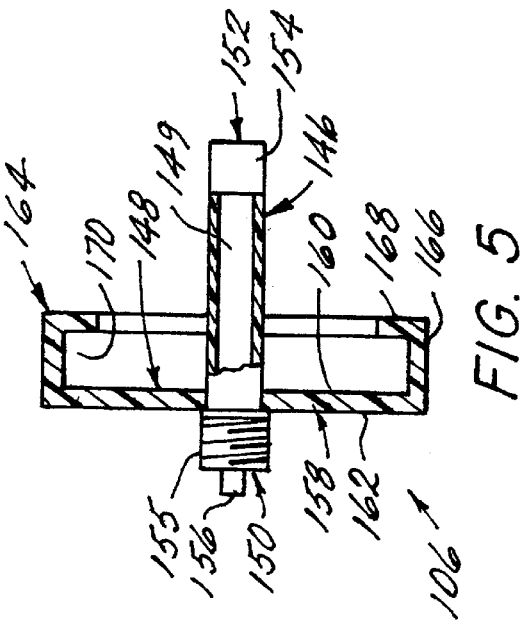
FIG. 5 is a cross-sectional side elevational view of a central line assembly of the device of FIG. 1.
Figure 4:
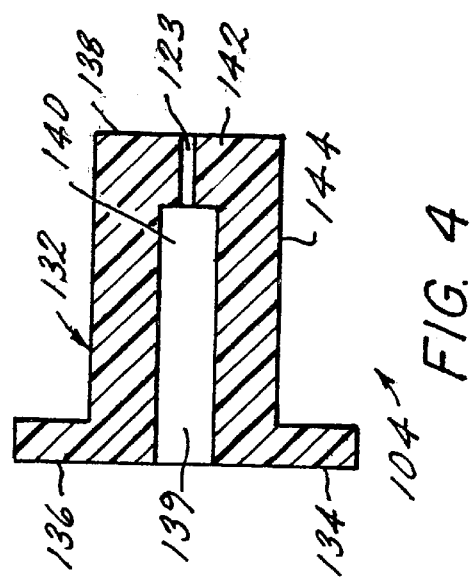
FIG. 4 is a cross-sectional side elevational view of a removable guide liner of the device of FIG. 1.

FIG. 1 is a cross-sectional elevated view of a closed system access device, shown generally at 100. Access device 100 includes a housing 102, a removable guide liner 104, and a line assembly 106. In one exemplary embodiment, central access device 100 comprises a central venous access device. It will be appreciated that central access device 100 has other potential uses including but not limited to: non-professional use of the central access device 100 by a layperson in a setting other than a healthcare facility; applications in veterinary medicine; uses in pathology; uses in dental medicine; applications in medical specimen collection and transportation; applications in collection, transportation, and disposal of hazardous bodily fluids (e.g., blood, cerebral-spinal fluid, pleural fluid, synovial fluid, peritoneal dialysate and amniotic fluid); and potential uses in medication administration during medical procedures.

Referring now to FIGS. 1–5. Housing 102 is shaped substantially as a cylindrical tubular member having an outer wall 108 and an interior 110. Housing outer wall 108 has a first end 112 and a second end 114. A first housing opening 116 is located at first end 112 and a second housing opening 118 is located at second end 114. A central wall 120 is mounted perpendicular to housing outer wall 108 such that interior 110 is divided into a first part 110A and a second part 110B. A first needle 122 is mounted such that it perpendicularly bisects central wall 120. First needle 122 extends into both first part 110A and second part 110B of housing interior 110. A preferred embodiment of housing 102 has needle 122 as a single lumen needle with one passage through the length of the needle 122 with openings at opposite ends thereof. First needle 122 passes through a syringe locking device 125 which is mounted to central wall 120 in second part 11 OB of housing interior 110. Second needle 124 is substantially L-shaped with a first portion 126 and a second portion 128. First portion 126 is mounted adjacent to and in intimate contact with first needle 122 in first part 110A of housing interior 110. Second portion 128 of second needle 124 is mounted perpendicular to first portion 126 and extends through and perpendicular to outer wall 108 terminating at a needle-less flush port 130. In a preferred embodiment, second needle 124 is a single lumen needle with one passage through the length of the needle 124 with openings at the non-joined ends of first portion 126 and second portion 128.

Removable guide liner 104 includes a guide liner body 132 and a flange 134. Guide liner body 132 comprises a substantially tubular member with a diameter slightly less than that of an inner surface 109 of outer wall 108 to permit insertion of removable guide liner 104 into housing 102 while maintaining significant friction to prevent slippage during usage.

Guide liner body 132 includes an exterior surface 144, a first end 136, and a second end 138. Guide liner body 132 includes a slot 140 formed therein, wherein the slot 140 has a diameter slightly larger than that of a body 146 to allow insertion of central line assembly 106 into removable guide-liner 104 while maintaining significant friction to prevent slippage during usage. Removable guideliner 104 is of universal design and may be used with a variety of central lines, as is discussed further below.

Second end 138 includes a capping member 142 mounted perpendicular to guide liner body 132 such that guide liner body 132 is closed at second end 138. Capping member 142 is preferably of a self-sealing type, such as a self-sealing membrane which seals after an object inserted therethrough is removed. Capping member 142 includes a groove 123 which runs perpendicularly through the center of capping member 142 to allow for the insertion of needle 122, as is discussed in further detail below. First end 136 includes an opening 139 which defines and is part of slot 140.

Flange 134 is preferably of an annular shape with an outer diameter substantially equal to an outer diameter of housing flange 115. Flange 134 is mounted perpendicular to guide liner body 132 at first end 136. Flange 134 contacts and seats against housing flange 115 when removable guideline 104 is inserted into housing first end 116 of housing 102.

Central line assembly 106 includes a body 146 and a locking member 148. Body 146 includes a channel formed therein and extending therethrough. In other words, in a preferred embodiment, the body 146 is tubular in nature with a channel 149 formed therein and extending from a first end 150 to a second end 152. Second end 152 preferably includes a self-sealing membrane 154 in communication with the channel, wherein the self-sealing membrane 154 is pierced by needle 122 when central line assembly 106 is inserted into removable guide liner 104 fitted into first end opening 116 of housing 102. First end 150 includes a connector 155 and a syringe tip 156 to facilitate connection with various venous access devices as is discussed further below. In one exemplary embodiment, connector 155 is of a threaded type which is designed to lockingly mate with an object while permitting fluid to pass therethrough from one member to another member.

Locking member 148 includes a top member 158 and a locking flange 164. Top member 158 includes a locking side 160 and a top side 162. Top member 158 is substantially annular in shape with a diameter greater than a diameter of flange 134. Top member 158 is perpendicularly bisected by body 146 such that connector 155 is mounted adjacent to and in intimate contact with top side 162 and syringe tip 156 extends perpendicularly away from top side 162 of locking member 148. First end 152 extends perpendicularly from locking side 160 of top member 158.

Locking flange 164 also includes a first locking flange member 166 and a second locking flange member 168. First locking flange member 166 is mounted to top member 158 perpendicular to locking side 162. Second locking flange member 168 is mounted perpendicular to first member 166 such that it extends towards body 146. First locking flange member 166 is of sufficient length to create a catch 170 between top member 158 and second locking member 168. Upon attaching central line assembly 106 to housing 102 fitted with removable guide liner 104, locking flange 164 snaps into a locked position with housing flange 115 and flange 134 captured in catch 170.

The uses of a closed system central access device 100 in accordance with this invention will now be discussed.

Figure 6:
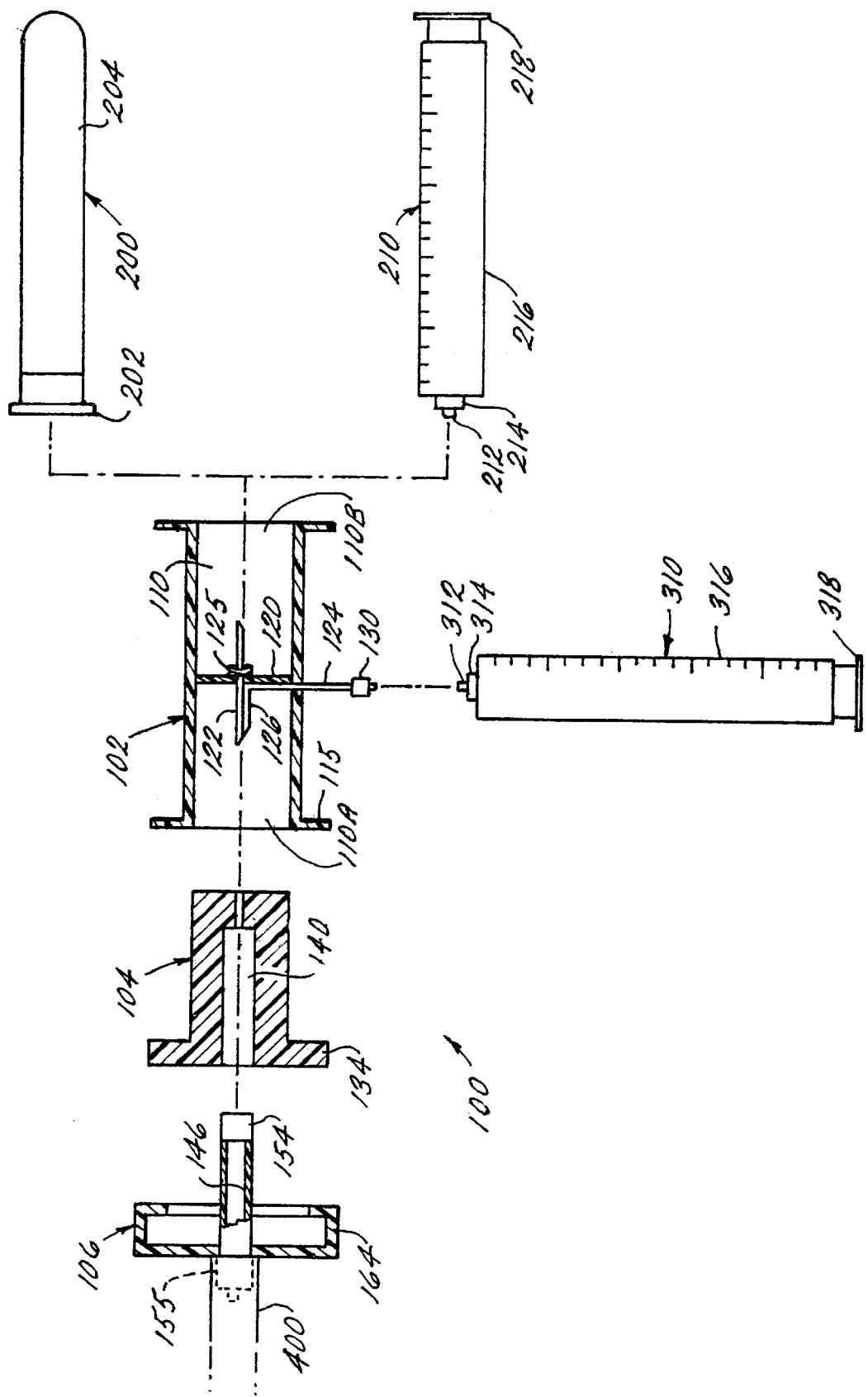
FIG. 6 is a cross-sectional side elevational view of an arrangement for using the device of FIG. 1 as a central venous line.

Referring now to FIGS. 1 and 6–8 in which access device 100 will be described as being used as a central venous access device. It being understood that the following uses for central access device 100 are merely exemplary in nature and do not limit the scope of the present invention. FIG. 6 is a cross-sectional exploded side elevational view of an exemplary method of drawing blood using the closed system central venous access device 100 of FIG. 1. Venous access device 100 is prepared by first inserting removable guide liner 104 into first part 110A of housing interior 110. Next, central line assembly 106 is inserted through first end 136 into slot 140 such that first needle 122 and second needle 124 pierce self-sealing membrane 154 and enter channel 149 of body 146. Central line assembly 106 is inserted into removable guide liner 104 until locking flange 164 snaps locks over both guide line flange 134 and housing flange 115. The venous access device is now assembled as is shown in FIG. 1. An access line 400 is fitted on screw connector 155 and connects the venous access device 100 to the vein of a patient. In an exemplary embodiment, the access line 400 comprises a central venous line. It being understood that access line 400 may comprise any number of members which are used to transfer bodily fluids. For example, the access line 400 shown in FIG. 6 is of a central venous line screw-type configuration which mates with connector 155. It is within the scope of the present invention that other accessing lines 400 may be used, including but not limited to a variety of ports or catheters for medical collection purposes, e.g., venous devices (Hickman catheter, PICC (peripherally inserted central catheter), midline catheter, Groshong catheter, Port-a-Cath); spinal catheters; shunts; or any other device for accessing bodily fluids depending upon the precise application for central access device 100.

A vacuum sealed test tube 200 is inserted into second part 110B of interior 110 of housing 102 such that needle 122 punctures a test tube cap 202 and enters a test tube body 204. Test tube cap 202 is preferably of a self-sealing membrane type. Pressure differential and gravity cause blood to be drawn through venous access line 400, into channel 149 of body 146, through first needle 122, and, finally, into test tube 200.

Alternatively, blood may be drawn into a syringe 210 by configuring venous access device 100 as described above and inserting syringe 210, instead of test tube 200, through second housing opening 118 into second part 110B of housing interior 110. Syringe 210 includes a syringe body 216, a syringe screw connector 214, a syringe tip 212 and a slidably contained compression member 218. Syringe 210 is inserted into housing 102 such that needle 122 enters syringe tip 212. Syringe screw connector 214 is mated with syringe locking device 125. Compression member 218 is then placed in the decompressed position drawing blood through venous access device 100 into channel 149 of body 146, through needle 122, and, finally, into syringe body 216.

If the liquid medication injected requires a fluid, such as saline to be injected before or after a blood draw, to flush the vein or the venous access line 400, such injection may be made using a second syringe 310. Syringe 310 includes a second syringe body 316, a second syringe tip 312, a second syringe screw connector 314, and a slidably contained second compression member 318. Injection fluid is placed into second syringe body 316 such that second compression member 318 is placed in the decompressed position. Second syringe tip 312 is inserted into needle-less flush port 130 and locked into position with second syringe screw connector 314. To administer fluid, second decompression member 318 is compressed injecting fluid through flush port 130, through second needle 124, into channel 149 of body 146, into venous access line 400 and finally into the patient's vein. A second fluid flush injection may be made by simply attaching to flush port 130 a new syringe containing fluid and following the procedure described above.

Figure 7:
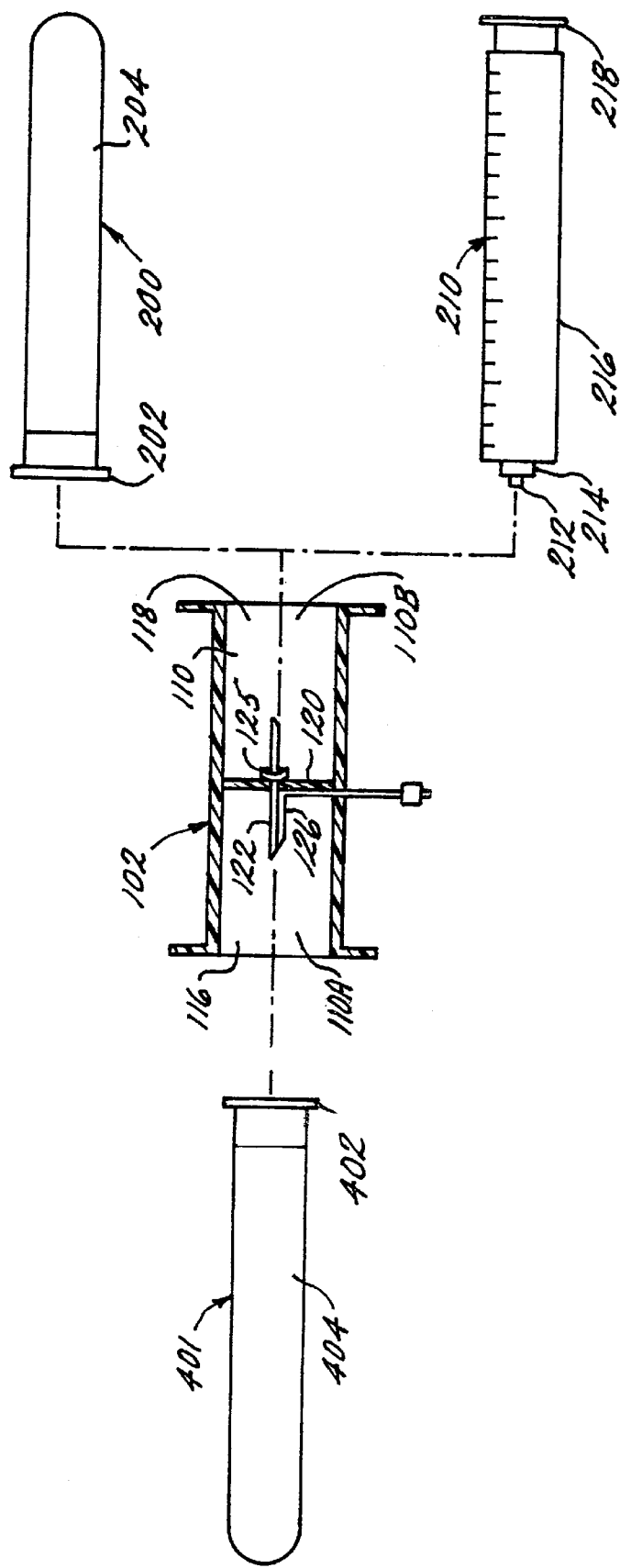
FIG. 7 is a cross-sectional side elevational view of an arrangement for transferring fluid into a test tube using the device of FIG. 1.

FIG. 7 is a side elevational view of an arrangement for transferring fluid using access device 100 of FIG. 1. To prepare access device 100 to transfer fluids, removable guide liner 104 and central line assembly 106 are detached from housing 102. Fluid contained in a test tube 200 or a syringe 210 may be transferred without needle stick and without contact with the fluid by first inserting either test tube 200 or syringe 210 into second part 110B of housing interior 110. Test tube 200 is inserted such that first needle 122 pierces test tube cap 202 and enters test tube body 204. Syringe 210 is inserted such that first needle 122 enters syringe tip 212 and then syringe body 216. Syringe screw connector 214 is mated with syringe locking device 125. Then, with test tube 200 or syringe 210 in place, vacuumed sealed receiving test tube 401 is inserted into first part 110A of housing interior 110 such that first needle 122 pierces receiving test tube cap 402 and enters receiving test tube body 404. Gravity and the pressure differential draw the fluid into receiving test tube 401.

Figure 8:
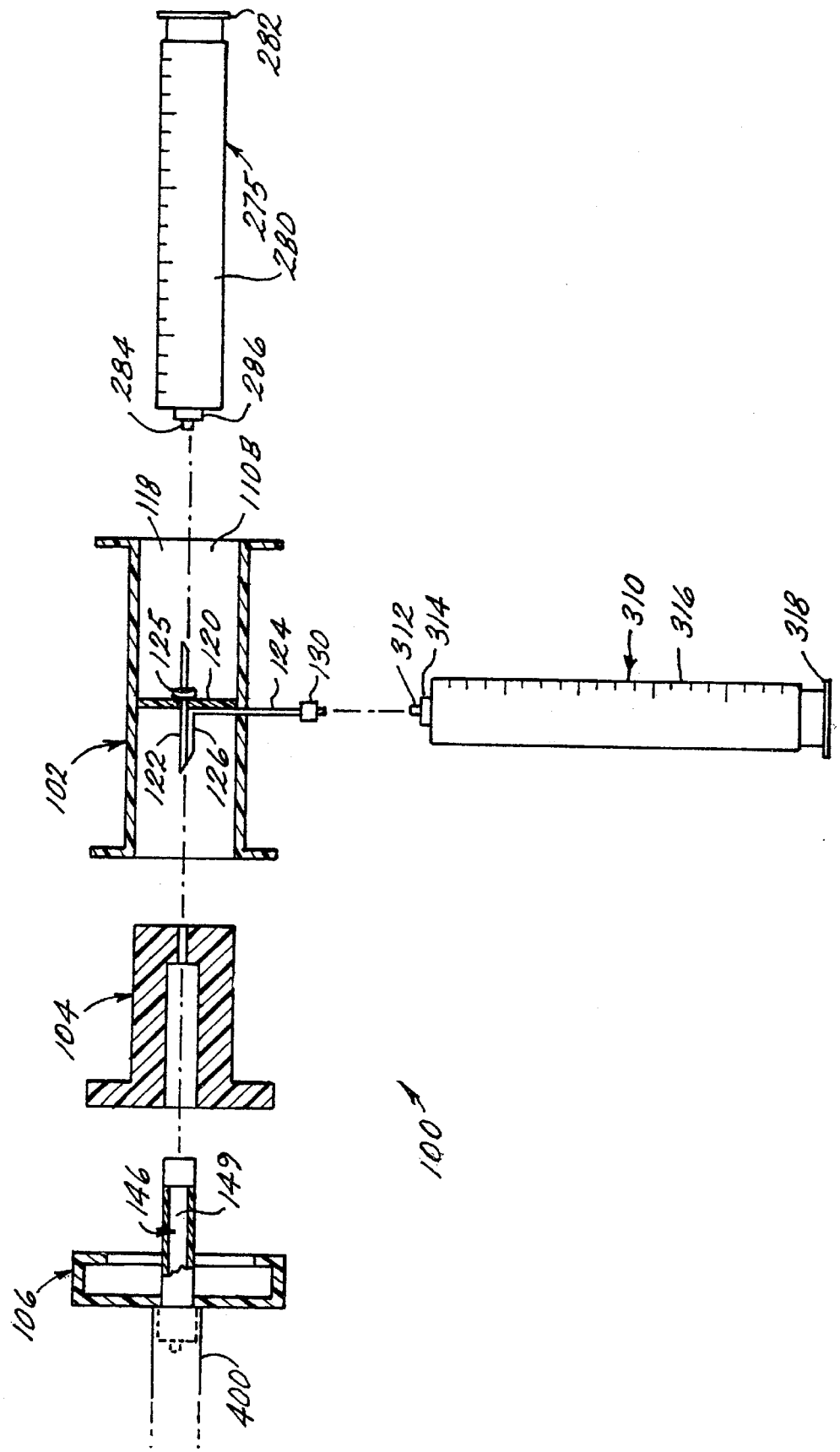
FIG. 8 is a cross-sectional side elevational view of an arrangement for administering liquid medication using the device of FIG. 1.

FIG. 8 is a side elevational view of an arrangement for administering liquid medication using the device of FIG. 1. Central access device 100 is prepared and connected to access line 400 as is described above with reference to FIG. 6. Liquid medication is placed in a medication syringe 275.

Medication syringe 275 includes a body 280 for holding a predetermined amount of medication, a compression member 282, a syringe tip 284, and a connector 286. Medication syringe 275 is inserted through second housing opening 118 into housing interior 110 such that first needle 122 enters syringe tip 284 and then syringe body 280. Connector 286 is mated with syringe locking device 125 securing syringe 275 to housing 102. Compression member 282 is compressed thereby injecting liquid medication through first needle 122, into channel 149 of body 146, through venous access implement 400 and into patient's vein.

If the liquid medication injected requires a fluid such as saline to be injected before or after administration of medication to flush the vein or the access implement 400, such injection may be made using a second syringe 310. Second syringe 310 includes a second body 316, a second tip 312, a second connector 314, and a slidably contained second compression member 318. Injection fluid is placed into second syringe body 316 such that second compression member 318 is placed in the decompressed position. Second syringe tip 312 is inserted into needle-less flush port 130 and locked into position with second syringe screw connector 314. To administer fluid second decompression member is compressed injecting fluid through flush port, through second needle 124, into channel 149 of body 146, into access line 400 and finally into patient's vein. A second fluid flush injection may be made by simply attaching to flush port 130 a new syringe containing fluid and following the procedure described above.

Figure 9:
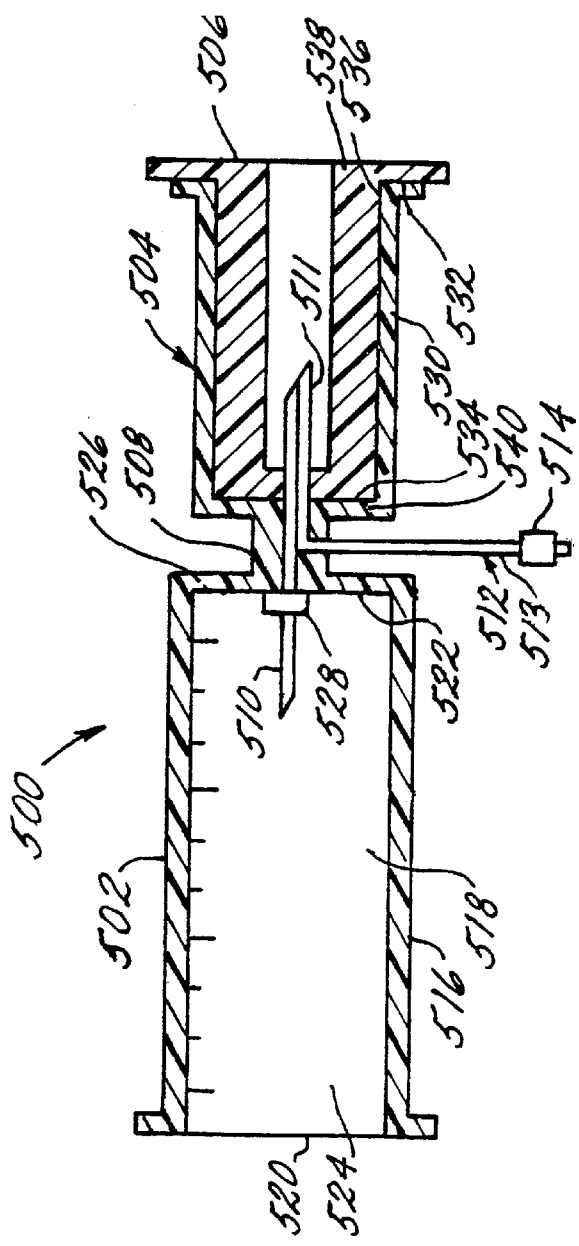
FIG. 9 is a cross-sectional side elevational view of a device according to a second embodiment of the present invention.

FIG. 9 is a cross-sectional elevational side view of an alternative embodiment of the device of FIG. 1. Alternative access device 500 includes a syringe body 502, a guide liner housing 504, a removable guide liner 506, and a connecting wall 508. Syringe body 502 is shaped substantially as a tubular member and includes an outer wall 516, an interior 518, a first end 520, and a second end 522. Outer wall 516 is of sufficient diameter such that a twenty to thirty cubic centimeter syringe may be inserted into interior 518. First end 520 includes opening 524. Second end 522 includes closing member 526 which is mounted perpendicular to outer wall 516 such that second end 522 is closed. Closing member 526 is perpendicularly bisected by a first needle 510. First needle 510 passes through a syringe locking device 528 which is mounted to closing member 526 extending into interior 518.

Guide liner housing 504 is shaped substantially as a tubular member and includes an outer wall 530, an interior 536, a first end 532, and a second end 534. Outer wall 530 is of diameter and thickness sufficient to allow for the insertion of removable guide liner 506 into interior 536. First end 532 includes an opening 538. Second end 534 includes a guide liner housing member 540 mounted perpendicular to outer wall 530 such that second end 534 is closed. Guide liner housing member 540 is perpendicularly bisected by first needle 510 and a second needle 512 adjacent to and in intimate contact with first needle 510. Removable guideliner 506 is preferably identical to that described above with reference to FIG. 4.

Connecting wall 508 joins syringe body 502 with guide liner housing 504. Syringe body 502 is mounted to connecting wall 508 at syringe closing member 526. Guide liner housing 504 is mounted to connecting wall 508 at guide liner housing member 540.

First needle 510 and second needle 512 are encased within alternative venous access device 500 to prevent needle stick and needle contamination. First needle 510 bisects connecting wall 508 and extends in either direction through syringe closing member 526 and guide line housing member 504 into syringe interior 518 and guide line housing interior 536, respectively. Second needle 512 includes a first portion 511 and a second portion 513. First portion 511 is mounted adjacent to and in intimate contact with first needle 510. Second portion 513 is joined perpendicularly to first portion 511 and extends outside of connecting wall 508. The free end of second portion 513 is fitted with needle-less flush port 514.

Alternative access device 500 may be used in accordance with the device of FIG. 1. Exemplary uses include blood drawing, liquid medication injection, and transfer of fluids from syringe to test tube, test tube to test tube, etc. These uses, with respect to the device of FIG. 1, are illustrated and described above with reference to FIGS. 6, 7, and 8. Alternative access device 500 is used in much the same manner. Guide liner housing 504 fitted with removable guide liner 506 may receive a central line assembly as described above with reference to FIG. 6. An access implement (not shown) may then connect alternative venous access device 500 to a patient's vein. Syringe body 502 may be used similarly to second part 110B of housing 102 of the device of FIG. 3 in that it may receive test tubes and/or syringes to facilitate blood draw, medication injection, or transfer of fluids. Alternatively, syringe body 502 may be used itself as a syringe by fitting it with a compression member, thus negating the step of attaching separate syringes in the uses described above. Thus, in this embodiment, syringe body 502 comprises an integral part of the alternative venous access device 500 and therefore eliminates the insertion of the separate syringe body into the device.

Figure 10:
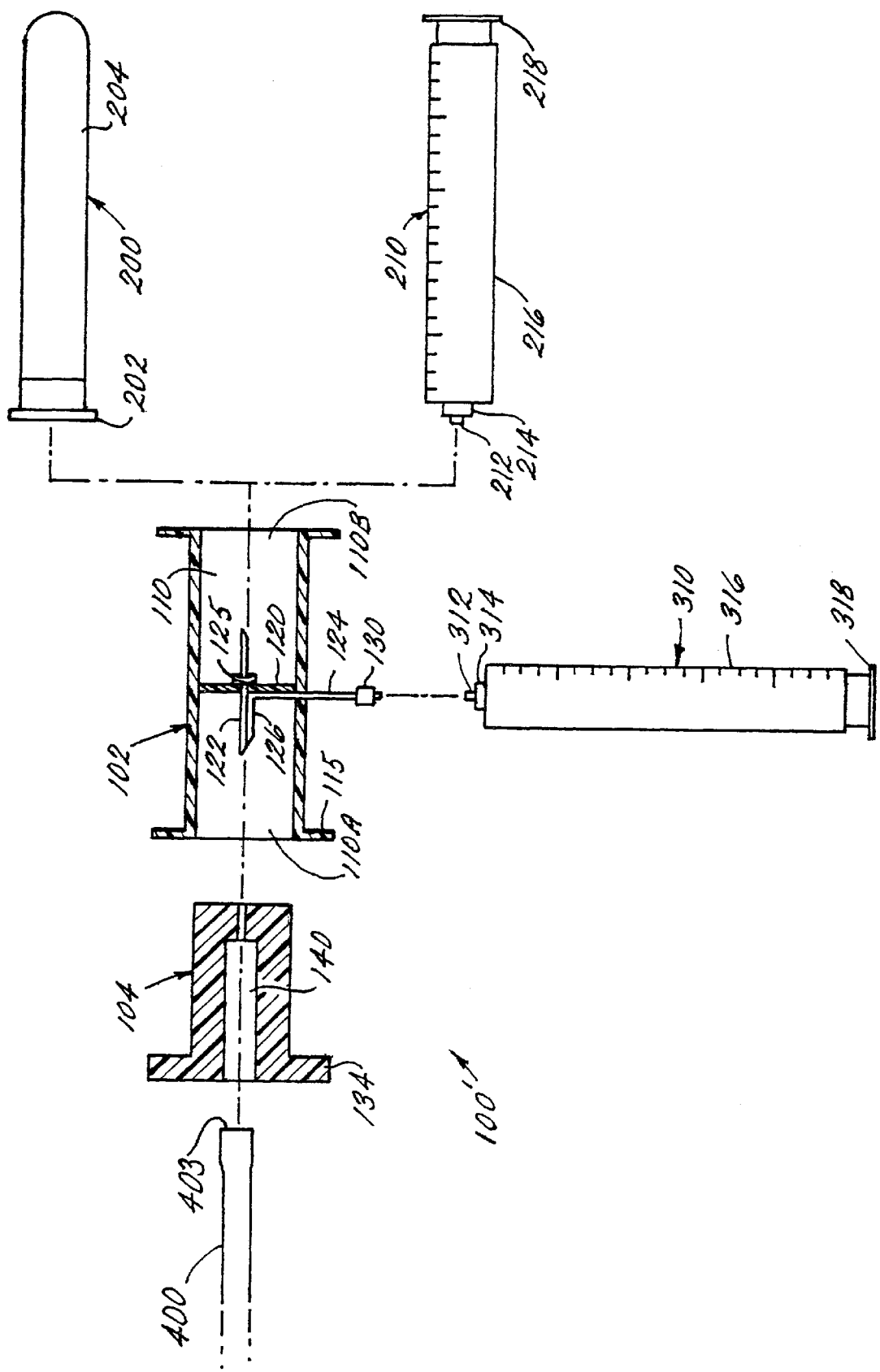
FIG. 10 is a cross-sectional side elevational view of a device according to another embodiment of the present invention.

Referring now to FIG. 10 in which a closed system access device 100' is shown. Access device 100' is similar to access device 100 with the exception that central line assembly 106 is eliminated and the access line 400 is connected directly to the first needle 122 and the first portion 126 of the second needle 124 without the use of central line assembly 106. In this embodiment, the access line 400 comprises an implement having a self-sealing tip 403, e.g., a central venous line with a self-sealing membrane. The access line 400 is inserted into the slot 140 and is directed towards the wall 120 resulting in the first needle 122 and first portion 126 piercing the self-sealing tip 403 causing the access line 400 to be securely retained within the housing 102.

In this embodiment when the central line assembly 106 is not used, the removable guide liner 104 is designed to be frictionally retained between the outer wall 108 of the housing 102. The insertion of the first needle 122 and the first portion 126 of the second needle 124 through the groove 123 helps to retain the removable guide liner 104 within the housing 102.

Figure 11:
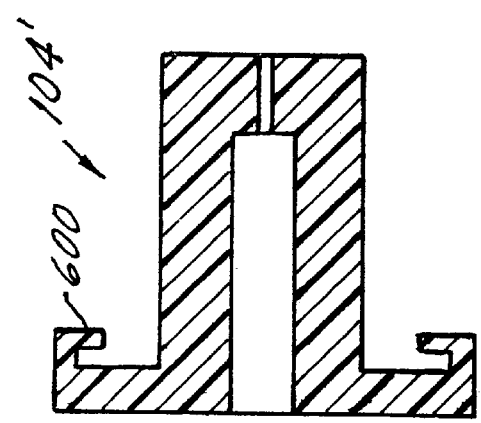
FIG. 11 is an alternative embodiment of a guide liner for use in the device according to the present invention.

Referring now to FIGS. 1 and 11 in which an alternative removable guide liner 104' is illustrated. The guide liner 104' is similar to the removable guide liner 104 with the exception that the guide liner 104' includes a locking tab 600 extending from the guide liner flange 134. The locking tab is designed to snap lock about the housing flange 115 to secure the guide liner 104' to the housing 102. In this configuration, the access implement 400 is disposed within the slot 140 and pierces the first and second needles 122, 124, respectively, of the housing 102.

Figure 12:
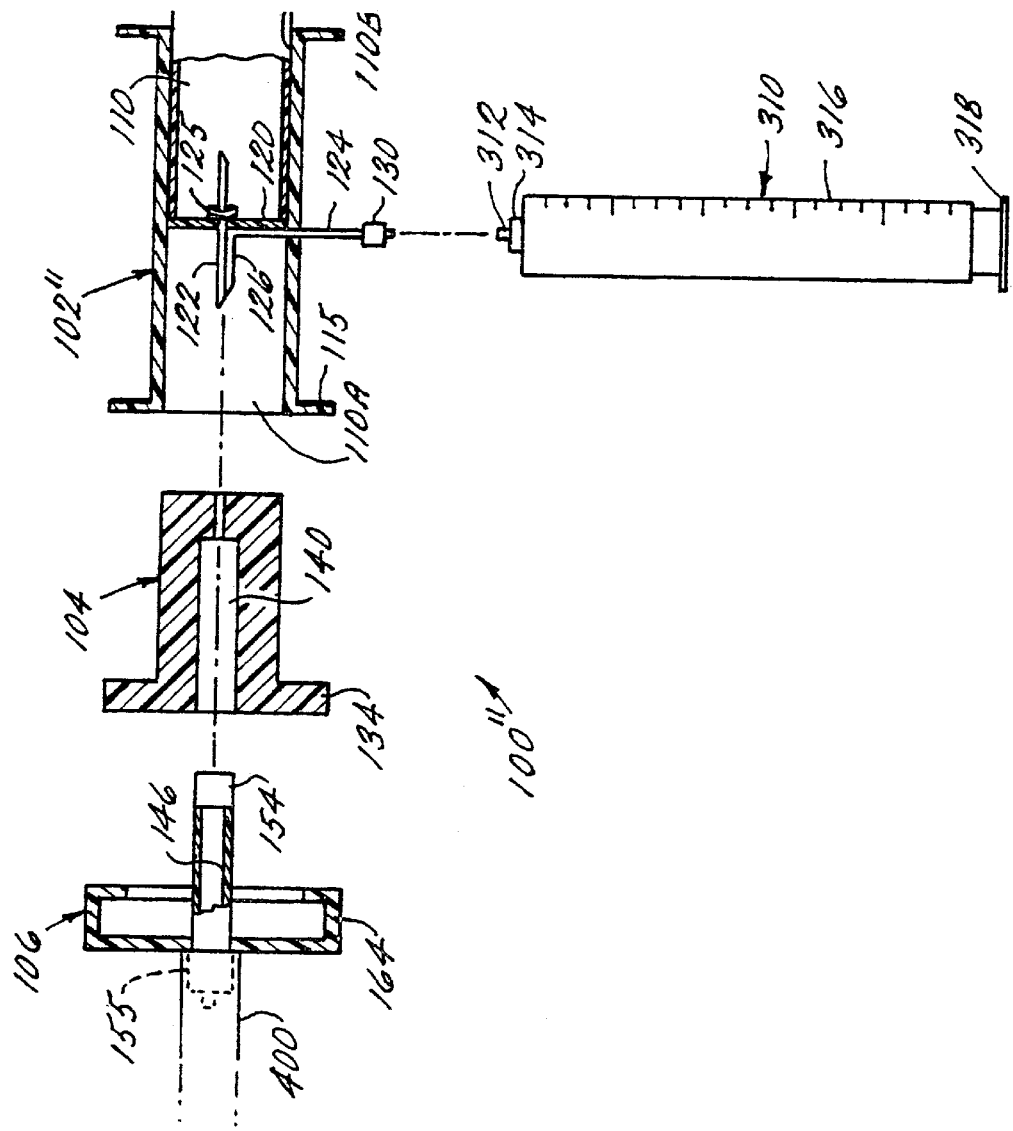
FIG. 12 is a cross-sectional side elevational view of a device according to another embodiment of the present invention.

Referring to FIG. 12 in which another embodiment of the present invention is illustrated. In this embodiment, a central access device 100" is provided. Central access device 100" comprises a device particularly suited for applications in medical specimen collection and transportation. Central access device 100" comprises housing 102" which includes a test tube 700 integrally formed therein. More specifically, the second part 110B of the interior 110 actually comprises an internal cavity of the test tube 700. In one exemplary embodiment, the test tube 700 is integrally formed as part of outer wall 108 so that the connector 125 and a portion of first needle 122 is disposed within the test tube 700. In this embodiment, the central access device 100" is designed to act as a collection and transportation device in that once a specimen is collected in the test tube 700 using the procedures set forth hereinbefore, the central access device 100" is disassembled until only the housing 102" including the test tube 700 remains. This one piece may then be packaged and transported to the desired location, such as a laboratory or testing facility. Thus by reducing the steps necessary for the collection and transportation of the bodily fluid, the present central access device 100" reduces the risk of contamination because it involves less steps and less human contact than previous procedures.

According to the present invention, a closed system central access device is provided. The device has a wide range of potential applications and is particularly well suited for procedures which require withdrawal of bodily fluids or administration of substances to a body. In one exemplary embodiment, the device comprises a closed system central venous access device. The device of the present invention would significantly decrease the risk of exposure from blood-borne pathogens to healthcare workers or the like during the following procedures which are merely illustrative and not limiting: injecting blood into a vacuum tube or specimen container, recapping syringes with needles containing blood by hand, removing needles from syringes containing blood by hand, using a needle to draw blood from a venous access device. Other intended uses for the devices disclosed herein are uses in medication administration and medical procedures, e.g., plasmaphoresis, blood donation, and synovial aspiration.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. A protective shielding assembly for use in transferring or receiving fluid from a patient, the assembly comprising:
   a housing having an outer wall and an intermediate wall extending between the outer wall of the housing, the intermediate wall partitioning the housing into a first section and a second section;
   a first needle extending from the first section to the second section of the housing through the intermediate wall, the first needle having a first portion disposed in the first section and a second portion disposed in the second section;
   a first connector disposed in the second section about the first needle for connecting a first member to the first needle in the second section;
   a second needle disposed at least partially in the first section of the housing and extending through the outer wall of the housing, the second needle terminating in a needle-less fluid port, the fluid port for fluid connection to a second member;
   a removable guide liner having a body including a first end, an opposing second end, and an outer wall complementary to the outer wall of the housing so that the removable guide liner is intimately received within the first section of the housing, the body having a guide slot formed therein and extending from the first end to an end wall proximate the second end, the end wall including an opening formed therein for receiving the first portion of the first needle and a portion of the second needle so that the first portion and the second needle extend into the guide slot, the guide slot receiving a third member which is fluidly connected to the first and second needles so that a fluid transfer may occur between the third member and at least one of the first and second members where the first and second needles are fully encased within the housing so as to protect the user from contact therewith.

2. The protective shielding assembly as set forth in claim 1, wherein the first member is selected from the group consisting of a sealed test tube, a syringe, and a collection device.

3. The protective shielding assembly as set forth in claim 1, wherein the first member has a second connector which mates with the first connector to securely retain the second member in the second section and from fluid communicating between the first member and the first needle.

4. The protective shielding assembly as set forth in claim 1, wherein the third member comprises a central line assembly including:
   an elongated body having a first end and a second end with a channel extending therethrough from the first end to the second end, the first end having a locking flange for locking the central line assembly to the guide liner and the housing, the second end being a capped end for selectively receiving the first portion of the first needle and the second needle, and
   a central line connected to the first end of the body so that the central line is in fluid communication with the first and second needles.

5. The protective shielding assembly as set forth in claim 1, wherein the housing comprises a substantially tubular member including a first annular flange at a first end thereof and a second annular flange at a second end thereof.

6. The protective shielding assembly as set forth in claim 1, wherein the removable guide liner comprises a substantially tubular member having an annular guide liner flange at the first end.

7. The protective shielding assembly as set forth in claim 4, wherein the capped end comprises a self-sealing membrane.

8. The protective shielding assembly as set forth in claim 4, wherein the central line assembly includes a third connector disposed at the first end of the elongated body, the third connector mating with a complementary fourth connector provided at one end of the central line, wherein the mating between the third and fourth connectors retains the central line to the elongated body and provided fluid communication between the central line and the channel.

9. The protective shielding assembly as set forth in claim 4, wherein the central line is selected from the group consisting of a central venous line, a catheter, and a shunt.

10. The protective shielding assembly as set forth in claim 1, wherein the fluid transferred is selected from the group consisting of blood, cerebral-spinal fluid, pleural fluid, synovial fluid, peritoneal dialysate, amniotic fluid, and liquid medication.

11. The protective shielding assembly as set forth in claim 1, wherein the second member comprises a syringe.

12. The protective shielding assembly as set forth in claim 1, wherein the third member is selected from the group consisting of a sealed test tube and a syringe.

13. A protective shielding assembly for use in transferring or receiving fluid from a patient, the assembly comprising:

a housing having an outer wall and an intermediate wall extending between the outer wall of the housing, the intermediate wall partitioning the housing into a first section and a second section, wherein the second section comprises a closed collection receptacle;

a first needle extending from the first section to the second section of the housing through the intermediate wall, the first needle having a first portion disposed in the first section and a second portion disposed in the closed collection receptacle;

a second needle disposed at least partially in the first section of the housing and extending through the outer wall of the housing, the second needle terminating in a needle-less fluid port, the fluid port for fluid connection to a first member;

a removable guide liner having a body including a first end, an opposing second end, and an outer wall complementary to the outer wall of the housing so that the removable guide liner is intimately received within the first section of the housing, the body having a guide slot formed therein and extending from the first end to an end wall proximate the second end, the end wall including an opening formed therein for receiving the first portion of the first needle and a portion of the second needle so that the first portion and the second needle extend into the guide slot, the guide slot receiving a third member which is fluidly connected to the first and second needles so that a fluid transfer may occur between the second member and at least one of the closed collection receptacle and first member where the first and second needles are fully encased within the housing so as to protect the user from contact therewith.

14. The protective shielding assembly as set forth in claim 13, wherein the closed collection receptacle comprises a sealed test tube.

* * * * *